United States Patent [19]

Gluckman et al.

[11] Patent Number: 5,710,127
[45] Date of Patent: Jan. 20, 1998

[54] USE OF GROWTH FACTOR IGF-I AND/OR IGF-II

[75] Inventors: Peter David Gluckman, Auckland; David James Mellor, Palmerston North, both of New Zealand

[73] Assignee: Pharmacia & Upjohn Aktiebolag, Stockholm, Sweden

[21] Appl. No.: 612,177

[22] Filed: Mar. 7, 1996

Related U.S. Application Data

[62] Division of Ser. No. 193,017, filed as PCT/SE93/00502, Jun. 7, 1993, Pat. No. 5,534,493.

[30] Foreign Application Priority Data

Jun. 8, 1992 [NZ] New Zealand ............ 243070
Jun. 7, 1993 [WO] WIPO ............ SE93/00502

[51] Int. Cl.$^6$ ............ C07K 7/10; A61K 38/00; A61K 37/36
[52] U.S. Cl. ............ 514/12; 514/21; 530/303; 530/309
[58] Field of Search ............ 514/12, 21; 530/303, 530/399

[56] References Cited

U.S. PATENT DOCUMENTS

| | | | |
|---|---|---|---|
| 5,482,926 | 1/1996 | Gluckman et al. | 514/12 |
| 5,534,493 | 7/1996 | Gluckman et al. | 514/12 |

FOREIGN PATENT DOCUMENTS

| | | |
|---|---|---|
| 222 551 | 11/1989 | New Zealand . |
| 223 520 | 4/1990 | New Zealand . |
| 226 132 | 2/1992 | New Zealand . |
| 236 641 | 2/1992 | New Zealand . |
| 227 857 | 4/1992 | New Zealand . |
| WO 89/05822 | 12/1988 | WIPO . |
| WO 90/15142 | 12/1990 | WIPO . |
| WO 91/12018 | 1/1991 | WIPO . |
| WO 91/03253 | 3/1991 | WIPO . |
| 9112018 | 8/1991 | WIPO . |
| 9203155 | 3/1992 | WIPO . |
| 9200754 | 1/1993 | WIPO . |

OTHER PUBLICATIONS

Heinz-Erian et al., Identification and In Situ Localization of the Insulin–Like Growth Factor II, Endocrinology (1991), p. 1769.
Schober et al., Endocrinology, vol. 126, No. 2, (1990), pp. 1125–1132.
Young et al., Insulin–Like Growth Factors and the Developing and Mature Rat Small Intestine: Receptors and Biological Actions, Digestion, 1990 (46), pp. 240–252.
Rivard et al., Negative Control by Sandostatin on Pancreatic and Duodenal Growth: A Possible Implication of Insulin–Like Growth Factor I, Regulatory Peptides (1991), vol. 34, pp. 13–23.
Grey et al., Insulin–Like Growth Factor II/Mannose–6–Phosphate Receptors Are Transiently Increased in the Rat Distal Intestinal Epithelium After Resection, Molecular and Cellular Endocrinology (1991), vol. 75, pp. 221–227.
Moessner et al., Chem. Abstract 108 (1988), 69411a.
Williams et al., Chem. Abstract 100 (1984), 133010h.
Koenuma et al., Insulin and Insulin–Like Growth Factor I Stimulate Proliferation of Metastatic Variants of Colon Carcinoma 26, Japan J. Cancer Res. 1989, Jan., vol. 80, No. 1, pp. 51–58 (Abstract).
Culouscou, Purification of a Colon Cancer Cell Growth Inhibitor and its Identification as an Insulin–Like Growth Factor Binding Protein, Cancer–Ref. (1991), Jun., Vol. 51, No. 11, pp. 2813–2819 (Abstract).

*Primary Examiner*—Cecilia J. Tsang
*Assistant Examiner*—P. Lynn Touzeau
*Attorney, Agent, or Firm*—Pollock, Vande Sande & Priddy

[57] ABSTRACT

The present invention relates to a composition comprising exogenous human or animal IGF-I or IGF-II or both or effective analogs thereof comprising foodstuff for oral administration wherein the foodstuff is selected from the group consisting of artificial milk, natural milk and colostrum.

6 Claims, No Drawings

USE OF GROWTH FACTOR IGF-I AND/OR IGF-II

This application is a divisional of U.S. patent application Ser. No. 08/193,017, filed as PCT/SE93/00502, Jun. 7, 1993, now U.S. Pat. No. 5,534,493.

The present invention relates to the use of IGF-I and/or IGF-II or effective analogues thereof for the manufacture of a medicament adopted for oral or any gastrointestinal route of administration for prevention or treatment of pancreatic disorders and insufficiency. It also relates to composition comprising exogenous human or animal IGF-t and/or IGF-II or effective analogues thereof comprising foodstuff for oral administration, preferably in admixture with artificial or natural milk or colostrum. The invention may be applied both in man and in animals.

INTRODUCTION AND PRIOR ART

Insulin-like growth factor1 (IGF-I) and insulin-like growth factor 2 (IGF-II) are peptides present in plasma and other body fluids. They show 64% homology of their primary sequences and comprise 70 and 67 amino acids respectively, including 3 disulphide bonds. They can stimulate growth of a wide range of cell types. IGF-I but not IGF-II mediates the effects of growth hormone on skeletal growth. Both IGF-I and IGF-II have been purified from human plasma and their complete amino acid sequences are known. Sequences with extensive homologies to human IGF-I and IGF-II are present in IGF-I and IGF-II purified from plasma of other species. IGF-I and IGF-II have both systemic and local effects and appear mostly associated with different specific binding problems, six of which are sequenced and are termed IGFBP1, IGFBP2, IGFBP3, IGFBP4, IGFBP5 and IGFBP6. These appear to modulate the biological functions and availability of IGF-I and IGF-II in both a positive and negative manner. Analogues with changed affinities for the binding proteins have been produced and changes of biological activities related to sequence variation have been found. Both IGF-I and IGF-II appear to act mainly by interactions with the IGF-type 1 receptor exposed on the outer surface of plasma membranes in many different cell types however relative specificity of action may be found because of the influence of binding proteins. Further IGF-II may have distinct actions as it alone binds to a distinct and unrelated type 2 receptor also found on cell membranes. Further binding of both IGF-I and IGF-II to insulin receptors also seems to be of importance.

Because of the scarcity of purified plasma IGF-I and IGF-II there was a great necessity to develop methodology for the commercial scale production of IGF-I and IGF-II. Nowadays such large scale production can readily be achieved by using recombinant DNA techniques. As a result of studies with preparations of recombinant DNA derived IGF-I it has been demonstrated that it promotes skeletal growth and skeletal muscle protein synthesis. Moreover IGF-i is also effective for the treatment or prevention of catabolic states (Swedish patent application SE 9002731-9). IGF-II has also been shown to antagonise some metabolic actions of IGF-I (Koea et al Endocrinology (1992). 130, 2423-2425). Ballard et al, WO 91/12018 have disclosed the therapeutic use of IGF-I for gastrointestinal disease or the treatment of the shortened gut after surgery. Ballard provides no evidence of activity or effects on pancreatic size or growth following oral administration.

It has previously been demonstrated that both type 1 and type 2 IGF receptors are present in the gastrointestinal tract and that oral IGF-I and IGF-II affect jejunal enzymes following repeated administration in older suckling rats, but no effect on intestinal growth was observed. (Young et al. Digestion 46, 1990, Suppl. 2, 240–252). It has also been reported that systemically (i.e. subcutaneous or intramuscular or intravenous) administered IGF-I can increase gastrointestinal weight, but pancreatic growth was not assessed. Heinze-Erian et al, Endocrinology, Vol 129, No 4, 1769, 1991 reports that there is an essential role for both IGF receptors in the regulation of cell mitogenesis and growth. Rivard Net al, Regul-Pept 1991, Jun. 11, Vol 34(1), 13–23 reports that intravenous injected IGF-I may have an effect on pancreatic and duodenal cell content of somatostatin and Grey Vet al, Mol-Cell-Endocrinol, 1991, Mar, Vol 75 (3), 221-7 suggest that IGF-II/M6P receptor levels are altered in the intestinal epithelium following gut resection.

Earlier studies have shown that there are IGF as well as insulin receptors on the pancreas cells, but as there are IGF receptors on all cell-types, this does not in any way suggest an action or a potential specificity of action.

There was thus not a priori reason to believe that IGF-I or IGF-II might be efficacious in the growth of the pancreas.

No effect of IGF-I or II on exocrine pancreatic function has been previously suggested and no studies of the effects of oral administration of the IGF's on pancreas have been previously suggested.

There is a need for a medicament adopted for oral or any gastrointestinal route of administration for prevention or treatment of pancreatic disorders and which also can be used for promoting pancreatic growth which is abnormal in the growth retarded animal.

It has now surprisingly been found that IGF-I and/or IGF-II or effective analogues thereof can be used for the manufacture of such a medicament.

THE INVENTION

The invention relates to the use of IGF-I and/or IGF-II or effective analogues thereof for the manufacture of a medicament adopted for oral or any gastrointestinal route of administration for prevention or treatment of pancreatic disorders.

The medicament also promotes pancreatic growth and is useful in the treatment of pancreatic insufficiency such as in intrauterine growth retardation, post partial pancreatectomy, cystic fibrosis and following pancreatitis.

Human or animal IGF-I or IGF-II can be used and may be given singly or in combination with each other or with other growth factors such as epidermal growth factor (EGF) for enhancing or improving the desired effect(s) of IGF-I, IGF-II or its effective analogues.

The invention relates to a composition comprising exogenous human or animal IGF-I and/or IGF-II or effective analogues thereof comprising foodstuff for oral administration, preferable artificial or natural milk or colostrum.

in animal either recombinant human IGF-I and/or IGF-II or IGF-I or IGF-II of other species (e.g. bovine, porcine) may be used either as an oral drench or as a supplement to artificial liquid or solid feeds.

Regarding the use for prevention or treatment of pancreatic disorders, the following uses are pointed out:

1) Promotion of pancreatic growth in men. In diseases associated with inadequate exocrine pancreatic function leading to fat malabsorption e.g. cystic fibrosis or in infants following partial/complete pancreatectomy for islet cell hyperplasia. In growth retarded infants who have disproportionately reduced pancreatic size.

2) Treatment of exocrine pancreatic deficiency In diseases such as cystic fibrosis, post pancreatectomy. Promotion of pancreatic development in growth retarded newbor.

4) Treatment in animals Promotion of growth of the pancreas to restore intestinal function of the growth retarded animals.

Preferably in man human IGF-I or IGF-II singly or in combination is used. The dose given could be 1 to 100 µg/kg/body weight per day in man and 1–1000 µg/kg, per day in animals. The preferred route of administration is by mouth either in aqueous buffer or other pharmacological composition or added to artificial feed, artificial or natural milk. Alternatively it may be installed more distally in the gastrointestinal tract for example by nasogastric tube or by duodenal tube.

In animal either recombinant human IGF-I or IGF-II of other species (e.g. bovine, porcine) may be used either as an oral drench or as a supplement to artificial liquid or solid feeds.

The claimed Composition can be used as a Supplement to Foodstuff

The foodstuff is preferably milk for the prevention or treatment of pancreatic disorders and for the promotion of pancreatic growth. Such a composition will at the same time promote nutrition, growth, and reduce the impact of gastrointestinal infection.

This is desirable in human infants with growth failure, prematurity of where there is difficulty in establishing oral feeding.

The use is particularly desirable in infant animals from large litters, on artificial feeds or where there is growth retardation present.

The invention also extends to a nutritionally acceptable composition for the supplementation of natural or artificial milk formula for human or animal use such that similar amounts of IGF-I and/or IGF-II or analogue are provided.

The peptide may be present in amounts sufficient to provide a dose rate of approximately 1 to 100 µg/kg body weight per day, preferably 1–10 µg/kg per day in man and 1–1000µg/kg per day in animals.

DETAILED DESCRIPTION OF THE INVENTION

The preferred form of the invention will now be described with reference to the following non-limiting example.

EXAMPLE 1

In a study 11 pigs not otherwise treated, pancreatic chemistry was ascertained after sacrifice immediately after birth. 6 of these were of normal size and 5 were intra uterine growth retarded (IUGR) at birth (Table 1). IUGR piglets were defined as those at least 2 standard deviations (SD) below the mean, whereas normal piglets had at birth weight within I SD of the mean.

TABLE 1

Chemical composition of the pancreas of the normal and growth retarded neonatal pig at birth (mean ± SEM)

|  | Normal (n = 6) | IUGR (n = 5) |
|---|---|---|
| Pancreatic weight (g) | 1.60 ± 0.10 | 0.57 ± 0.04* |
| Pancreatic Wt:body Wt (g/kg) | 1.21 ± 0.05 | 0.96 ± 0.04* |
| Protein (mg/g tissue) | 170 ± 4.7 | 160.8 ± 11 |
| RNA (mg/g tissue) | 6.20 ± 0.37 | 6.05 ± 0.33 |
| DNA (mg/g tissue) | 6.81 ± 0.71 | 7.66 ± 0.51 |
| Total DNA (mg) | 10.8 ± 0.9 | 4.3 ± 0.3* |
| Protein:DNA (mg/mg) | 25.9 ± 1.7 | 21.0 ± 0.4 |
| RNA:DNA ration (mg/mg) | 0.93 ± 0.06 | 0.80 ± 0.06 |

*$p < 0.05$

Results presented in this table show that the pancreas was disproportionately smaller in IUGR piglets than that in normal piglets. The retardation of pancreatic development observed in the IUGR piglets was mainly due to hypoplasia less cell number as total pancreatic DNA content was lower in those animals. histological examination showed reduction in all cell types.

EXAMPLE 2

Studies were performed in newborn piglets, that were raised for 24 hours following birth with a commercial infant milk formula (SMA Gold Cap; John Wyeth & Bro (NZ) Ltd) containing undetectable (<1 ng/ml) levels of IGF-I or IGF-II or with the same formula supplemented with either 2 µg/ml of recombinant human IGF-I or recombinant human IGF-II (provided Kabi Pharmacia AB, Sweden). 7 piglets received each treatment. The piglets were from 7 litters and each litter provided on one formula fed, one formula plus IGF-I fed and one formula plus IGF-II fed piglet. The piglets had statistically similar birth weights. After birth the piglets were fed by bottle 20 ml/kg every 2 hours for the first 12 hours, then 40 ml/kg every 4 hours thereafter until slaughter. Prior to slaughter the animals were injected with BDRU to enable calculation of cellular mitotic rate. The animals were thereafter slaughtered at 24 hours after birth for histological evaluation.

TABLE 2

Mean body-weight and weights and physical dimensions of digestive organs in 24 hour old piglets raised on an infant formula with or without addition of IGF-I or IGF-II. (n = 7)

|  | Control | IGF-I | IGF-II |
|---|---|---|---|
| Birth Weight (kg) | 1.286 | 1.317 | 1.295 |
| Final Weight (kg) | 1.318 | 1.328 | 1.320 |
| Stomach weight (g/kg)# | 5.02 | 5.11 | 4.99 |
| Pancreas weight (g/kg)# | 1.23 | 1.41** | 1.37* |
| Small intestine |  |  |  |
| Weight (g/kg)# | 29 | 32 | 29 |
| Length (cm/kg)# | 310 | 293 | 323 |
| Mitotic index (cells/crypt labelled) | 6.93 | 9.09*** | 8.63*** |
| Large intestine |  |  |  |
| Weight (g/kg)# | 6.2 | 6.3 | 6.4 |
| Length (cm/kg)# | 69 | 66 | 72 |

Adjusted for the birth weight.
*$p < 0.05$;
**$p < 0.01$:
***$p < 0.001$

TABLE 3

Chemical compositions of the pancreas and the proximal jejunal mucosa.

|  | Control | IGF-I | IGF-II |
|---|---|---|---|
| Pancreas: (n = 7) | | | |
| Weight (g/kg)# | 1.23 | 1.41** | 1.37* |
| Protein (mg/kg)# | 153 | 1.82** | 182* |
| RNA (mg/kg)# | 11.6 | 14.2* | 13.5* |
| DNA (mg/kg)# | 4.4 | 6.1* | 5.9* |
| Protein:DNA | 35.3 | 31.5 | 32.0 |
| RNA:DNA ratio (mg/mg) | 2.67 | 2.43 | 2.40 |
| Proximal jejunal mucosa: (n = 5) | | | |
| Weight (g/kg)# | 5.712 | 6.754 | 6.147 |
| Protein (mg/kg)# | 583 | 623 | 559 |
| RNA (mg/kg)# | 28.9 | 33.7 | 31.0 |
| DNA (mg/kg)# | 25.0 | 30.4 | 28.1 |
| Protein:DNA | 23.0 | 20.5 | 20.0 |
| RNA:DNA ratio (mg/mg) | 1.14 | 1.12 | 1.11 |

Adjusted for the birth weight.
*$p < 0.05$
**$p < 0.01$

These observations provide clear evidence that in neonatal animals oral administration of IGF-I and IGF-II are selectively active to promote growth of the pancreas.

Histological examination showed the hyperplasia (increase of number of cells) of the pancreas involved the exocrine pancreas. The effect on the pancreas was particularly marked compared to other aspects of the gastrointestial system. The increase in pancreatic size is due to an increase in cell number but not the cell size as the DNA content increases but protein:DNA ratio remained constant. These observations show clearly that oral IGF-I or IGF-II promotes pancreatic hyperplasia.

Light microscopy showed this was due to an increase in pancreatic exocrine cells dominant cell of the pancreas responsible for the production of fluids and enzymes necessary for absorption. The data clearly show activity of oral administered IGF-I or IGF-II even in the presence of artificial milk.

Evidence suggests differential effects of IGF-I and IGF-II such that specific effects will be possible by selection of a suitable dose and preferential use of IGF-I or IGF-II or their admixture.

EXAMPLE 3

Further histological data was obtained from the histological examination of sections of the pancreases obtained for example 2.

The cellular features of the same pancreases from the control and the IGF-I and IGF-II treatment groups were therefore evaluted quantitatively. All cell counts related to the area of the visual field minus connective tissue, blood vessels etc. The features examined were (1) with regard to all cells, total cells per unit area, mean area per cell and the BrdU (bromdeoxyuridine, a marker for DNA synthesis) mitotic index, (2) with regard to endocrine cells, the numbers per unit area of insulin, glucagon and somatostatin secreting cells per unit area, and the total for the three types, and (3) by difference, the number of exocrine cells per unit area.

Endocrine cells of different types were identified by standard immunohistochemical techniques employing specific antibodies for insulin, glucagon and somatostatin. The total number of endocrine cells was determined in each case by adding the numbers for insulin, glucagon and somatostatin stained cells.

Results

1. There was a 14.6% increase in pancreatic weight with IGF-I ($p<0.01$); associated with that was a 6% increase in mean cell size and an 11% increase in mitotic index. This suggests that both hypertrophy and hyperplasia was induced by IGF-I.

2. There was an 11.4% increase in pancreatic weight with IGF-II ($p<0.05$); associated with this was a 5% increase in mean cell size but no increase in mitotic index. This suggests IGF-II induces hypertrophy alone.

The results from the histological examination are presented in Table 4.

TABLE 4

Features of the pancreas (x ± SEM)

|  | Control | IGF-I | IGF-II |
|---|---|---|---|
| Total cells | | | |
| Cells/unit area (no/mm$^2$) | 9942 ± 493 | 9373 ± 354 | 9443 ± 347 |
| Area/cell (μml$^2$/cell) | 102 ± 5.4 | 108 ± 4.7 | 107 ± 3.5 |
| BrdU index (no/mm$^2$) | 14.8 ± 3 | 16.5 ± 2.7 | 14.9 ± 1.8 |
| Endocrine cells | | | |
| Insulin (no/mm$^2$) | 692 ± 73 | 741 ± 68 | 633 ± 112 |
| Glucagon (no/mm$^2$) | 1015 ± 90 | 960 ± 83 | 1065 ± 108 |
| Somatostatin (no/mm$^2$) | 57 ± 13 | 69 ± 17 | 48 ± 10 |
| Total Endocrine cells (no/mm$^2$) | 1765 ± 109 | 1770 ± 91 | 1746 ± 174 |

We claim:

1. Composition comprising exogenous human or animal IGF-I or IGF-II or both or effective analogs thereof and foodstuff for oral administration wherein the foodstuff is selected from the group consisting of artificial milk, natural milk and colostrum.

2. Composition according to claim 1 for prevention or treatment of pancreatic disorders comprising exogenous human or animal IGF-I or IGF-II or both or effective analogues thereof.

3. The composition of claim 1 which comprises exogenous human or animal IGF-I.

4. The composition of claim 2 which comprises exogenous human or animal IGF-I.

5. The composition of claim 1 which comprises exogenous human or animal IGF-II.

6. The composition of claim 2 which comprises exogenous human or animal IGF-II.

* * * * *